United States Patent
Higgins et al.

(10) Patent No.: US 12,296,158 B2
(45) Date of Patent: May 13, 2025

(54) INTRAVASCULAR BLOOD PUMP AND HEMODYNAMIC SUPPORT SYSTEM WITH BLOOD FLOW PULSATILITY VALIDITY MONITORING AND INVALIDITY DETECTION WITH ALARM

(71) Applicant: Cardiovascular Systems, Inc., St. Paul, MN (US)

(72) Inventors: Joseph P. Higgins, Minnetonka, MN (US); Benjamin D. Haselman, Dayton, MN (US); Gregory B. Ingersoll, Minneapolis, MN (US); Matthew W. Tilstra, Rogers, MN (US); Brian P. Schmalz, Minnetonka, MN (US); Kayla J. Eichers-Lundberg, Minneapolis, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 450 days.

(21) Appl. No.: 17/658,290

(22) Filed: Apr. 7, 2022

(65) Prior Publication Data
US 2022/0387778 A1    Dec. 8, 2022

Related U.S. Application Data

(60) Provisional application No. 63/208,283, filed on Jun. 8, 2021, provisional application No. 63/208,253, filed
(Continued)

(51) Int. Cl.
*A61M 60/148*    (2021.01)
*A61M 60/546*    (2021.01)
(Continued)

(52) U.S. Cl.
CPC ........ *A61M 60/148* (2021.01); *A61M 60/546* (2021.01); *A61M 60/562* (2021.01); *A61M 60/857* (2021.01); *A61M 2205/3334* (2013.01)

(58) Field of Classification Search
CPC ................ A61F 2/82; A61F 2210/0014; A61F 2250/001; A61M 1/3663;
(Continued)

(56) References Cited

U.S. PATENT DOCUMENTS 6,135,943 A * 10/2000 Yu ....................... A61M 60/422
600/16
2009/0099406 A1    4/2009 Salmonsen et al.
(Continued)

OTHER PUBLICATIONS

International Search Report and Written Opinion issued in related PCT Application No. PCT/US2022/71611, dated Jul. 18, 2022.

*Primary Examiner* — Jon Eric C Morales
(74) *Attorney, Agent, or Firm* — Kagan Binder, PLLC (57) ABSTRACT

A medical device with an implantable blood pump and a control and sensing unit configured to determine the flow rate generated by the blood pump when driven by an electric motor, wherein the flow rate is determined using peak-to-peak current data generated by the electric motor and, in some cases, associated heart rate data. In some embodiments, the validity of pulsatility of the resulting blood flow is determined and, if out of predetermined limits, an alarm may be actuated.

25 Claims, 10 Drawing Sheets

Related U.S. Application Data on Jun. 8, 2021, provisional application No. 63/208,276, filed on Jun. 8, 2021.

(51) Int. Cl.
*A61M 60/562* (2021.01)
*A61M 60/857* (2021.01)

(58) Field of Classification Search
CPC .......... A61M 2205/3334; A61M 60/13; A61M 60/148; A61M 60/174; A61M 60/183; A61M 60/216; A61M 60/232; A61M 60/242; A61M 60/414; A61M 60/422; A61M 60/523; A61M 60/546; A61M 60/592; A61M 60/81; A61M 60/857; A61M 60/894; A61M 60/896
See application file for complete search history.

(56) References Cited

U.S. PATENT DOCUMENTS

| | | |
|---|---|---|
| 2015/0031969 A1 | 1/2015 | Khair |
| 2019/0321531 A1 | 10/2019 | Cambronne et al. |

\* cited by examiner

INTRAVASCULAR BLOOD PUMP AND HEMODYNAMIC SUPPORT SYSTEM WITH BLOOD FLOW PULSATILITY VALIDITY MONITORING AND INVALIDITY DETECTION WITH ALARM

CROSS-REFERENCE TO RELATED APPLICATIONS

This application claims the benefit of U.S. Provisional Application No. 63/208,253, filed Jun. 8, 2021 and entitled INTRAVASCULAR BLOOD PUMP AND HEMODYNAMIC SUPPORT SYSTEM WITH BLOOD FLOW PULSATILITY VALIDITY MONITORING AND INVALIDITY DETECTION WITH ALARM. U.S. Provisional Application No. 63/208,276, filed Jun. 8, 2021 and entitled INTRAVASCULAR BLOOD PUMP AND HEMODYNAMIC SUPPORT SYSTEM WITH FLOW RATE DETERMINATION and U.S. Provisional Application No. 63/208,283, filed Jun. 8, 2021 and entitled INTRAVASCULAR BLOOD PUMP AND HEMODYNAMIC SUPPORT SYSTEM WITH FLOW RATE VALIDITY MONITORING AND INVALIDITY DETECTION, the entireties of which are hereby incorporated by reference.

STATEMENT REGARDING FEDERALLY SPONSORED RESEARCH OR DEVELOPMENT

Not Applicable

FIELD OF THE INVENTION

Generally, embodiments of the present invention related to hemodynamic support systems comprising blood pumps, and determination of flow rate through the blood pump and validity of pulsatility.

BACKGROUND OF THE INVENTION

Figure 1:
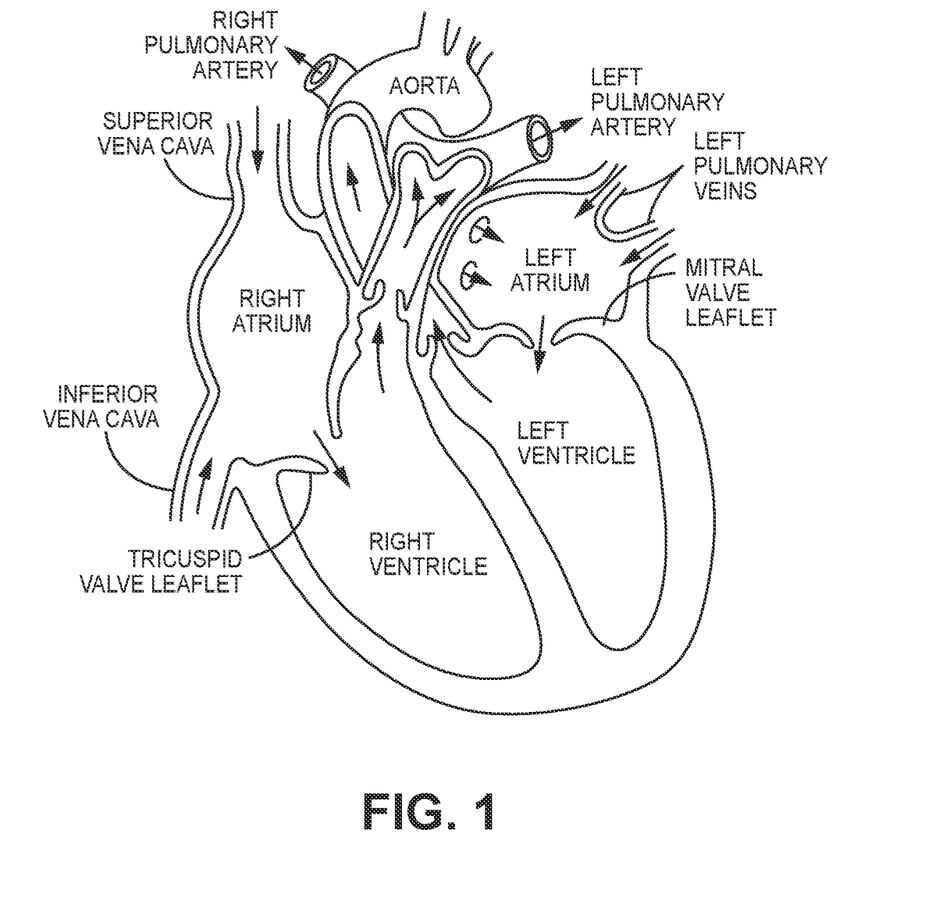
FIG. 1 is a cross-sectional view of the human heart.

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. Temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Figure 2:
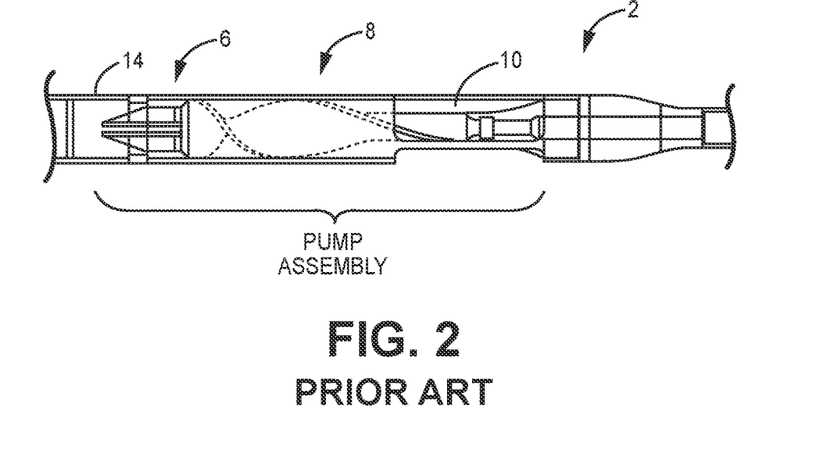
FIG. 2 is a cutaway view of a prior art blood pump.

Known ventricle assist devices ("VAD"), including LVAD and RVAD (right ventricular assist) devices, whether with integrated motor (long-term support use) or an external motor (temporary support use), generally comprise the following elements mounted within a housing, listed in order from the inflow end to the outflow end: an inflow aperture(s); a stationary inducer, also known as a flow straightener; a rotational impeller, and a stationary diffuser and/or outflow structure; and an outflow aperture(s) as shown in the exemplary prior art pump and/or impeller assembly cross sectional and cutaway view of FIG. 2.

In FIG. 2, a known VAD device 2 is oriented with the inflow end (distal end) on the left side of the drawing and the outflow end (proximal) on the right side, so that the incoming blood flow in the ventricle enters the device housing through the inflow aperture(s) (not shown), flows through the lumen or channel defined by the surrounding housing 14, ultimately entering the impeller/pump assembly. There, the incoming blood encounters the stationary inducer 6 before being urged forward by the rotating impeller 8. The blood flow may then be modified by a stationary diffuser and exits into the aorta via the housing's outflow aperture(s) 10. This exemplary device may comprise an integrated motor (long-term support) or may comprise an external motor with interposed drive cable (temporary support).

Hemodynamic support devices thus comprise intravascular blood pumps that assist the heart in pumping blood though the patient's vasculature on a short-term or temporary basis or a long-term basis. In all cases, it is necessary to understand how much blood is flowing through the device when operating at changing pump impeller speeds and/or hemodynamic conditions such as blood pressure and pulse rate.

Various mechanisms have been proposed to determine blood flow rate. For example, U.S. Pat. No. 7,010,954 comprises a reference look-up table for a particular blood pump that compares the blood flow rates obtained with corresponding motor speeds during the reference data generation stage.

There is no known direct measurement of flow rate in intravascular blood pumps. There is also no known direct measurement of pressure at the device. Therefore the blood flow rate must be estimated using the only two methods of feedback available for data processing: motor speed and motor current.

US 2020/0360582 ("582") discloses a reference look-up table or graph estimating blood flow based on motor current, but specifically teaches that "it is not possible to reliably determine the flow based on a measured motor current at a given motor speed once the blood pump is implanted in a patient's body." Accordingly, the '582 publication thus requires a motor current deviation value (calculated as the deviation from the reference motor current value) for the patient-specific motor current value measured during in-patient use. Ultimately, this motor current deviation value is applied to the measured patient-specific motor current value to arrive at a corrected flow rate.

Other known solutions require individual device and/or patient-specific calibration processes to be executed before accurate results may be obtained.

Applicants have discovered that a robust flow rate determination may be obtained using the peak-to-peak motor current for a given motor speed at any point, including but not limited to when the blood pump is implanted in the patient's body. Further, Applicants have discovered that the determined flow rate does not require individual device calibration or patient-specific calibration. The calibration-free flow rate determination described herein has been determined to be independent of the absolute motor current- which also varies with temperature, drive shaft friction, and other unknown and time-varying characteristics of the device.

Moreover, Applicants have discovered that it is possible to monitor peak-to-peak motor current for each heart cycle and determine if the monitored peak-to-peak current for each heart cycle is within a predetermined range or whether the monitored peak-to-peak current is determined to be below a predetermined lower threshold on a cycle-by-cycle basis while the medical device, e.g., blood pump, is implanted and operating within the patient.

Still further, Applicants have discovered that the pulsatility of the resulting blood flow through the implanted blood pump may be monitored for sufficient magnitude of current peak-to-peak values or magnitudes and/or heart rate. If, e.g., one or more current peak magnitudes is determined to be below a predetermined current peak low threshold, and/or the associated heart rate is determined to be outside of predetermined upper and lower thresholds, then the pulsatile blood flow may be determined to be invalid. The invalidity may result in actuation of an alarm to alert the operator.

The inventions disclosed herein address these, inter alia, issues.

DETAILED DESCRIPTION OF THE INVENTION

Generally, various embodiments of the present invention are directed to determining blood flow rate through an intravascular blood pump within a hemodynamic support device or system such as a ventricular assist device ("VAD") such as a left ventricular assist device ("LVAD") or a right ventricular assist device ("RVAD").

Figure 3:
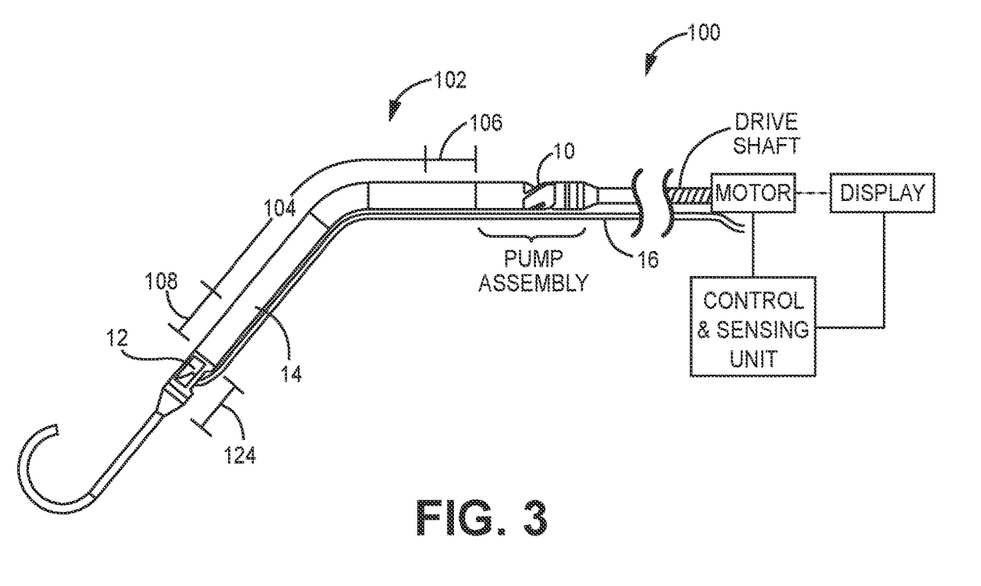
FIG. 3 is a side view of an exemplary blood pump of the present invention.

Referring now to FIG. 3, an exemplary temporary support LVAD blood pump 100 is illustrated, with inflow apertures 12 on the left side of the illustration (distal side of the blood pump 100) and outflow apertures 10 on the right side (proximal side of the blood pump 100) of the illustration. The motor is shown as located on the proximal end of the device outside the patient's body and connected with a rotational drive shaft that is, in turn, connected with the impeller or rotor 8 or pump assembly. However, as described above and as is well known in the art, the motor may be located within the housing of the device itself, wherein the motor is typically mounted on the proximal side of the rotor 8 or impeller or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 may be positioned alongside the exterior of the device until reaching the inlet apertures 12 where it enters inlet apertures and continues through the distal flexible and curved element. Thus, the guide wire 16 does not pass through the impeller or rotor 8 or pump assembly. In alternative embodiments, guide wire 16 may traverse down the center of housing cannula 14, passing by the rotor 8 or impeller or pump assembly and exit housing through slots in the bearing housing proximal to outlet apertures 10.

With reference generally to the Figures, the device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Alternatively, another embodiment of the housing H of exemplary device 100 in FIG. 3 is non-expandable. Regardless, the inventive flow rate determination is not dependent upon knowing the housing, or defined lumen or channel, diameter.

Figure 4:
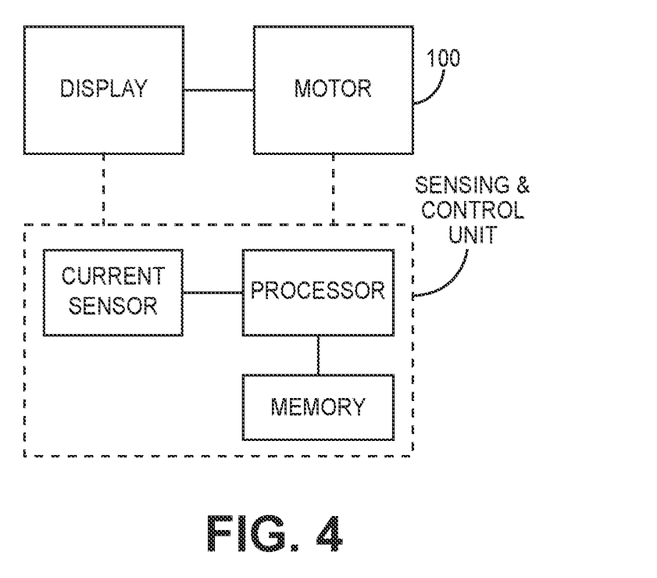
FIG. 4 is a block diagram of a system according to one embodiment of the present invention.

With continued reference to FIG. 3, and in combination with FIG. 4, an exemplary current sensing and control or processing unit comprising a control sensor is illustrated in operative communication with the exemplary device 100, and specifically with motor, and in further operative communication with a processor and, in some embodiments, with a display which is also in operative communication with the device 100 and/or motor. Processor may be in communication with a memory element where the flow rate equations and coefficients resulting from the described process, and programmed instructions implementing aspects of the described process may be stored.

Processor may be configured and/or adapted to comprise instructions for carrying out the various steps described herein, and adapted to receive current data related to the motor. The skilled artisan will recognize that the required current data may be obtained with a current sensor as in FIG. 4. Moreover, the artisan will also recognize that a specific memory element may not be required and that any required data to be stored may be stored within e.g., the processor's instructions which may be further stored within the processor itself. All such modifications are within the scope of the present invention. What is required is that the system be configured and/or adapted to obtain current data generated by the motor and execute the described process steps on a running, i.e., continuous, or a semi-continuous, basis with subsequent display of at least some of the current readings and/or flow rate determinations.

Determining blood flow rate based on motor current at a given rotational speed generally comprises use of the oscillating motor current signal at a given motor speed to calculate an estimated flow rate. During the systolic phase of the cardiac cycle, the aortic valve is open and the pressure differential between the inlet windows and outlet windows is close to zero. During diastole, the aortic valve is closed and the ventricular pressure is near zero (the ventricle is refilling), therefore the pressure differential between the inlet and outlet windows is approximately equal to aortic diastolic pressure. As the pump continues to run throughout the cardiac cycle, the pressure differential oscillates between approximately zero and the unknown aortic diastolic pressure.

At a given motor speed, varying pressure differentials are manifested as varying motor currents (the amount of work done by the impeller changes based on the flow rate, and the flow rate changes with pressure). By evaluating current changes throughout the cycle (the amplitude of the current wave), an estimation of average flow rate through the device can be calculated.

This estimation or determination of flow rate discussed herein is independent of the absolute motor current—which also varies with temperature, drive shaft friction, and other unknown and time-varying characteristics of the device—and is predominantly a function of the peak-to-peak height of the current waveform at a given motor speed.

As used herein, peak-to-peak means the amplitudes of current peaks, including but not limited to adjacent peaks, of the current waveform and/or the current magnitudes at the relevant waveform peaks.

The general steps in arriving at the robust flow rate determination mechanism discussed herein comprise:
Test data collection, analysis, and algorithm preparation;
Signal filtering;
Cycle synchronization and peak-to-peak detection;
Final flow estimation; and
Coefficient determination.

(1) Test Data Collection, Analysis, and Algorithm Preparation.

In order to begin estimating or determining flow rate using only motor current at a given motor speed, a test bench setup was used in order to create a pulsatile pressure environment across the pump cannula as is seen in the clinical environment. The test setup is such that the clinical conditions (blood pressure, pulse rate, native flow rate, etc.) may be adjusted, and the flow rate through the cannula may be independently measured by an external flow sensor. Using this test setup, a matrix can be created which correlates measured flow rate (at a given motor speed) to the peak-to-peak height of the current waveform. This matrix can be built across multiple pressures, pulse rates, and device samples to assess and account for component and process variability. Using this data, an algorithm and sets of mathematical coefficients can be prepared which use motor speed and motor current (specifically the peak-to-peak amplitude of the current waveform) to estimate flow rate through the cannula.

(2) Signal Filtering.

For both coefficient determination (see step 5) and during runtime of the embedded algorithm, to effectively process the motor current data, the data is fed through a low-pass filter to eliminate any high-frequency noise that may arise from onboard power supplies, interference coupling into cables, characteristics of the motor drive itself, analog-to-digital conversion, etc. The filter used in an existing embodiment of the invention is a 64-tap, low-pass, finite impulse response (FIR) filter with a cutoff frequency of 10 Hz for a sampling rate of 50 Hz.

(3) Cycle Synchronization and Peak-to-Peak Detection.

The filtered motor current is analyzed in order to identify points where the cardiac cycle begins. In the existing embodiment, this is performed by calculating a running average of the motor current and noting points where motor current is increasing and its value crosses over the value of its own average (in the same way that the "beginning" of a sine wave is generally taken to be the point where the signal is increasing and crosses zero). With these points known, all of the speed and motor current samples in one cardiac cycle can be treated as a set, and determining the minimum, maximum, and average value is straightforward.

(4) Final Flow Estimation.

Measurements of experimental devices show a strong correlation between motor current and device flow. Further, the point of maximum flow correlates with the point of maximum current and minimum (approximately zero) differential pressure across the device. So the flow through the device at the point of maximum current in a cycle is taken to be dependent only on motor speed and not dependent on pressure, absolute current, temperature, heart rate, or other unknowns. Based on this, the peak flow in the cycle is calculated from the average of the motor speed during the cycle (which is nearly constant over one cycle) and a linear function with constant, predetermined coefficients (see step 5 below).

Other motor current values in the cycle are taken not as absolute values but as a difference from the peak value for the cycle. Then for each sample, a decrease in flow relative to the peak flow is determined from the decrease in current from the peak current using a quadratic function with constant, predetermined coefficients.

In this manner, the minimum, maximum, and average flow for one cardiac cycle are calculated, and can be displayed to the user with or without additional averaging or other conditioning.

(5) Coefficient Determination.

To determine the coefficients for the two equations used for flow estimation, experimental datasets with direct measurements of device flow, motor current, and motor speed are collected over a matrix of device, nominal motor speed, systolic/diastolic pressure, native flow rate (the blood flow generated by the patient's heart without VAD support), and heart rate. Analysis of these datasets independently and in aggregate show that a single set of coefficients is sufficient to estimate flow with adequate accuracy without calibrating each device and without zeroing or periodically adjusting device parameters during operation of the device (i.e. calibration to the patient is not required). Embodiments of the device may display the estimated or determined flow rate.

Figure 5:
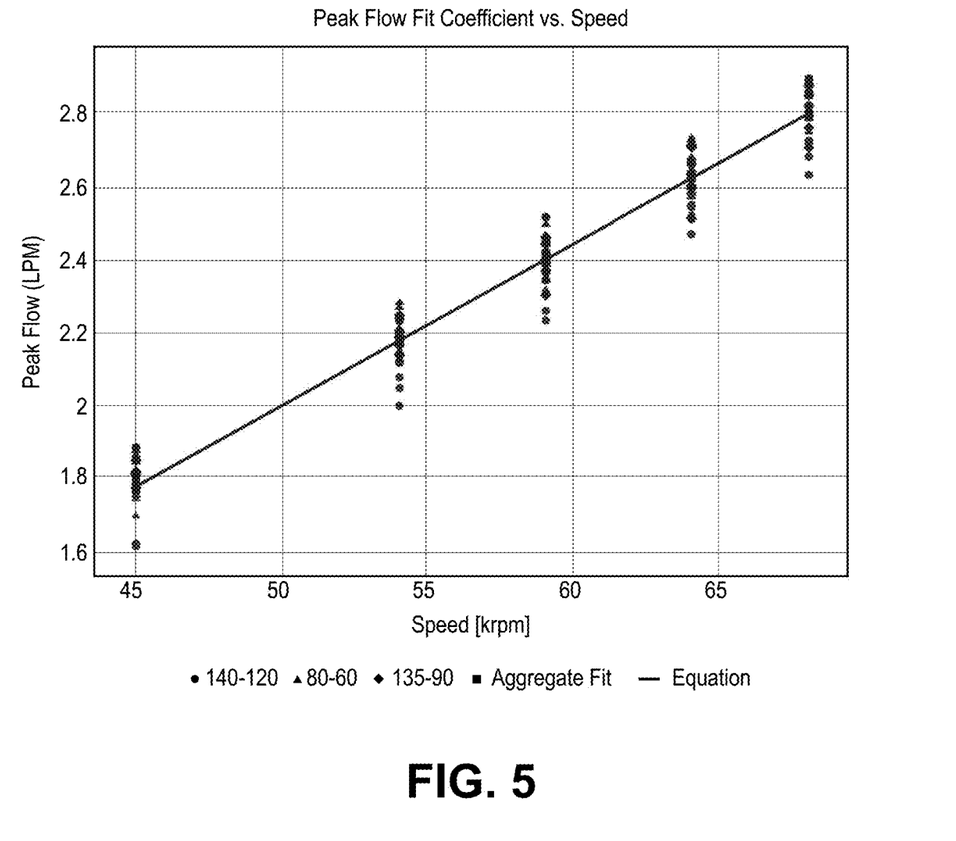
FIG. 5 is an exemplary graph of peak flow vs speed of one embodiment of the present invention.
Figure 6:
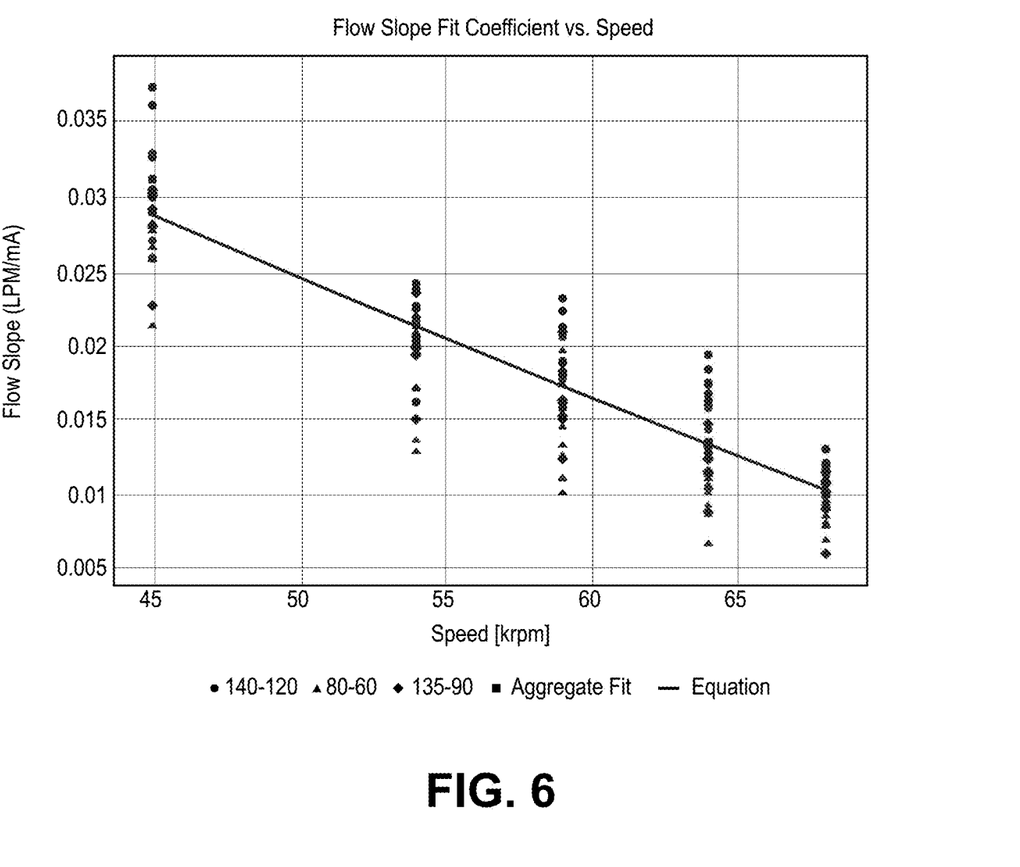
FIG. 6 is an exemplary graph of flow slop vs speed of one embodiment of the present invention.
Figure 7:
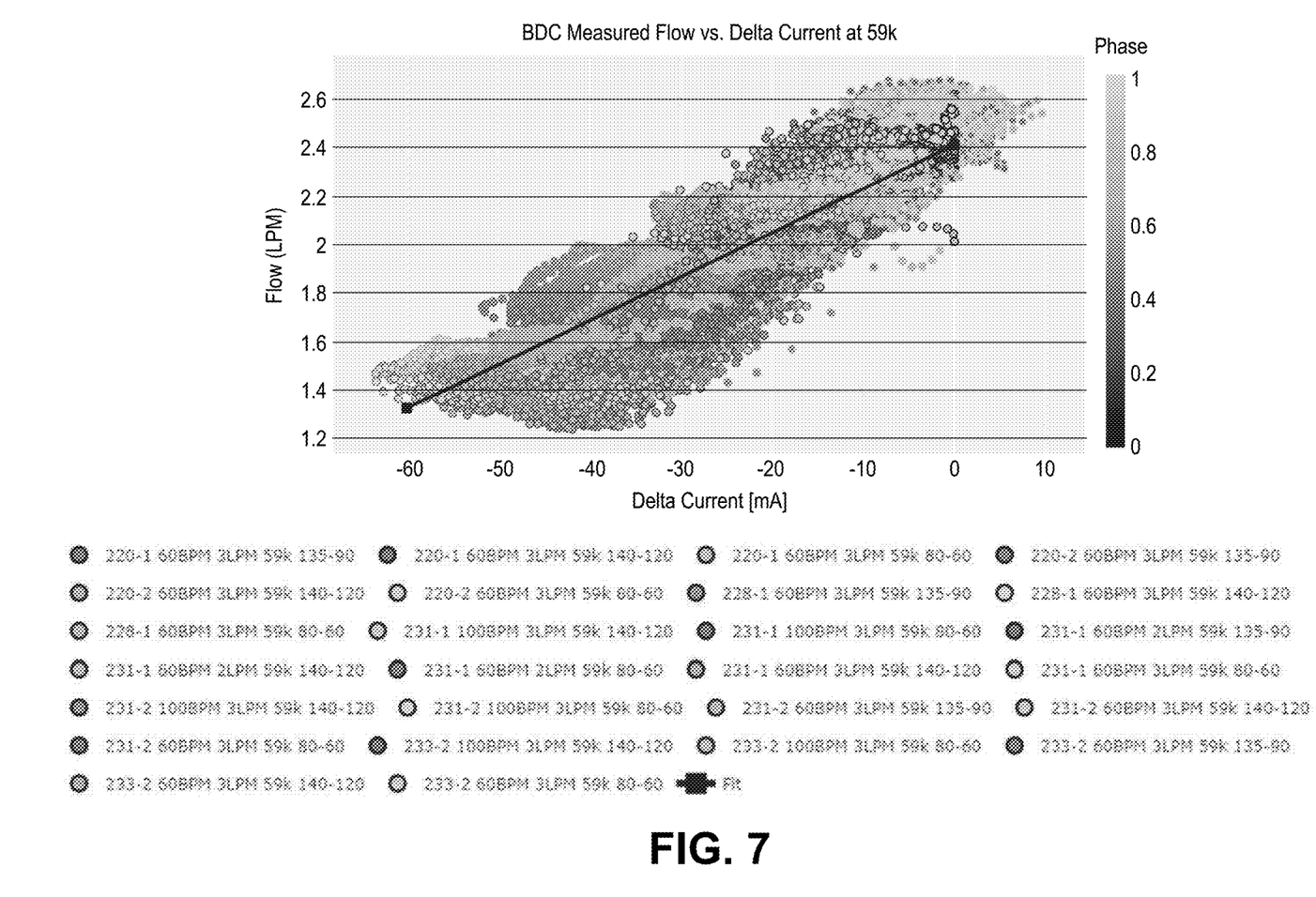
FIG. 7 is an exemplary best-fit line for flow vs delta current of one embodiment of the present invention.

Example plots for a group of datasets are shown below. The first plot demonstrates that the peak flow ($Q_{peak}$) through the device is linear with motor speed and is not significantly dependent on other variables. The second plot shows that the change in flow for a change in motor current (dQ/dI) has a dependence on speed that is fit with a quadratic function. The third plot shows that for a given speed but across devices and physiological pressures, the change in flow vs. change in current can be approximated as linear where the slope of the line varies with speed.

The data shown in FIGS. 5, 6 and 7 was collected over a matrix of three systolic/diastolic pressure regimes (80/60, 135/90, and 140/120 mmHg), two heart rates (60 BPM, 100 BPM), five operating speeds (45, 54, 59, 64, and 68 kRPM), and six devices (designated 220-1, 220-2, 228-1, 231-1, 231-2, and 233-2). FIG. 5 illustrates the peak flow fit coefficients vs speed. FIG. 6 illustrates flow slope fit coefficients vs speed. FIG. 7 illustrates an exemplary best fit line of measured flow vs delta current at 59 kRPM.

Aggregating and then fitting this data results in the following two equations for estimating flow during operation:

$$Q_{peak}(\omega) = 0.043993440\omega - 0.19271438$$

$$\frac{dQ}{dI}(\omega) = 1.9577226 \times 10^{-6}\omega^2 - 0.0010280405\omega + 0.071081653$$

where flow (Q) is in liters per minute (LPM), current (I) is in milliamps (mA), and speed ($\omega$) is in kRPM.

The artisan will readily appreciate and recognize that coefficients and resulting equations described above are merely exemplary and that other coefficients may be applied, depending on the experimental setup and type of hemodynamic support device that is used. In addition, the skilled artisan will recognize that the above approach may be applied to a hemodynamic support device with an unexpandable housing or with an expandable housing or a hemodynamic support device with an integrated and implanted motor or a device having an external motor with a drive shaft. Further, the process described herein may be completed for devices and blood pumps of various sizes, impeller types, and other various differential characteristics, wherein the resulting flow rate determination equations are reflective of the specific differential characteristics as in, e.g., different device models. However, it is to be understood that a preferred embodiment comprises the resulting flow rate equations to apply generally to blood pumps having common characteristics, e.g., device models.

Figure 8:
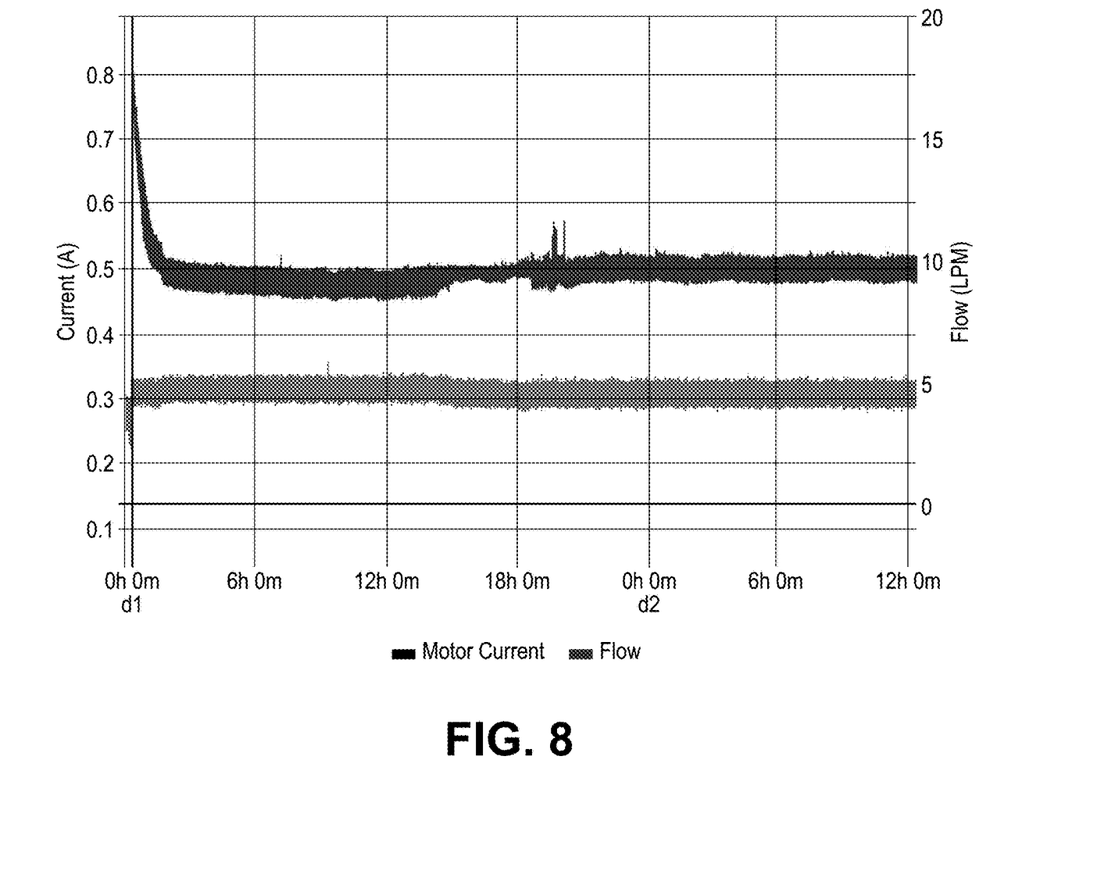
FIG. 8 illustrates exemplary "total flow" according to one embodiment of the present invention, defined as the combined native heart-generated blood flow plus VAD or blood pump device-induced flow, with the corresponding motor current illustrated in the bottom data set.

FIG. 8 illustrates "total flow", defined as the combined native heart-generated blood flow plus VAD or blood pump device-induced flow. The corresponding motor current is shown in the bottom data set. This data indicates that the total blood flow is pulsatile, wherein the pulsatility is due to the cardiac cycle and not necessarily as a consequence of the motor current inducing pulsatility, though such an approach is also within the scope of the present invention.

However, over time, the data illustrates a generally constant blood flow baseline or average, with the exception of the significant current decrease at the beginning of the test run. In addition, the current increases slightly on average about halfway through the run at or around approximately 16 hours. The total flow rate indicates a very small decrease at the same time period, corresponding with the slight increase in current, but continues to run at a relatively constant baseline or average flow rate.

Figure 9:
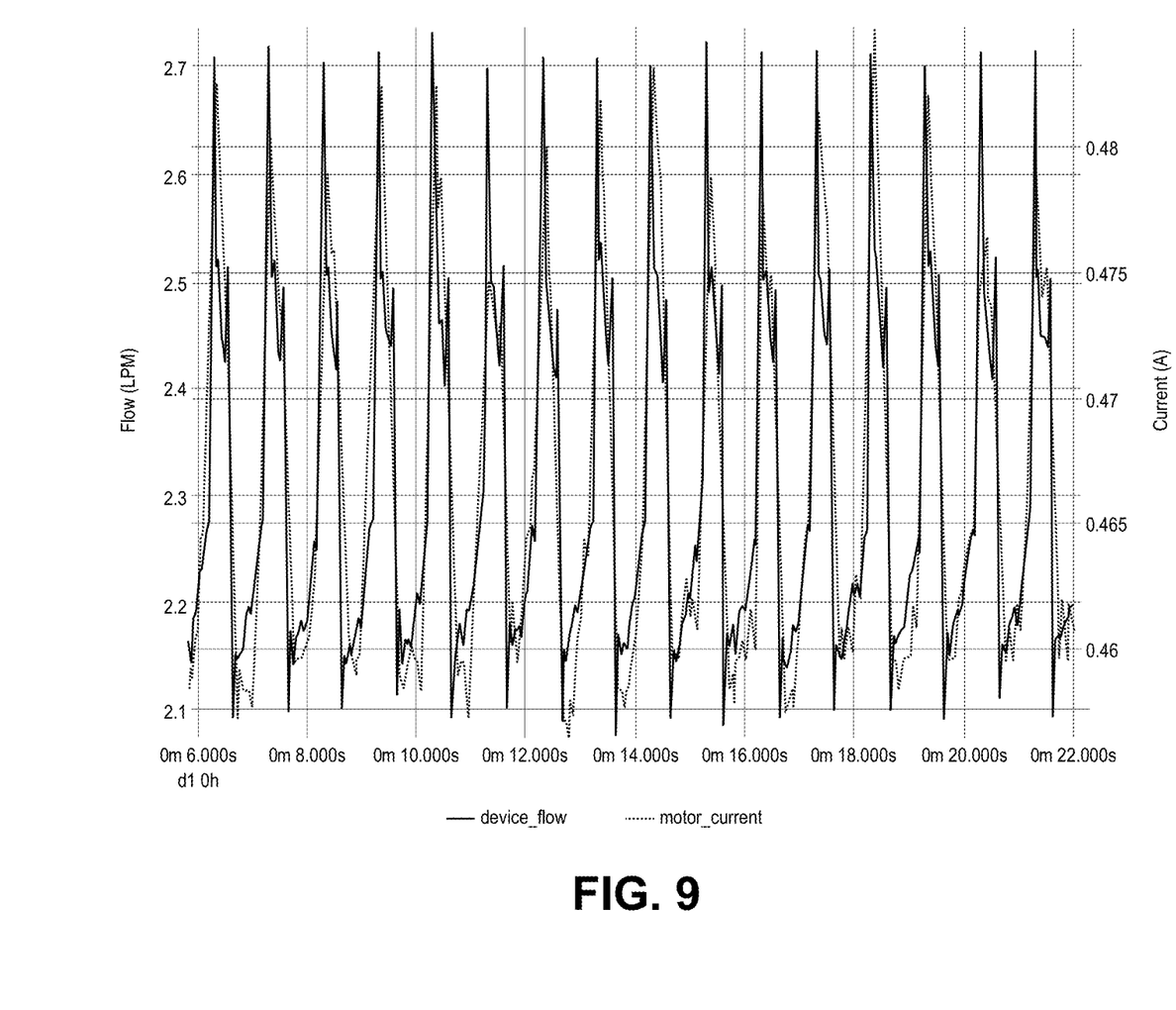
FIG. 9 illustrates the exemplary close correlation between peak-to-peak blood flow through the blood pump device and the peak-to-peak motor current of one embodiment of the present invention.

The data plot of FIG. 9 is a close-up of the close correlation between peak-to-peak blood flow through the blood pump device and the motor current.

Flow Rate Validity Monitoring and Invalidity Detection

The present invention further monitors the generated flow rate for validity, detects invalidity and, if invalidity is sufficiently persistent, then actuates an alarm.

Figure 10:
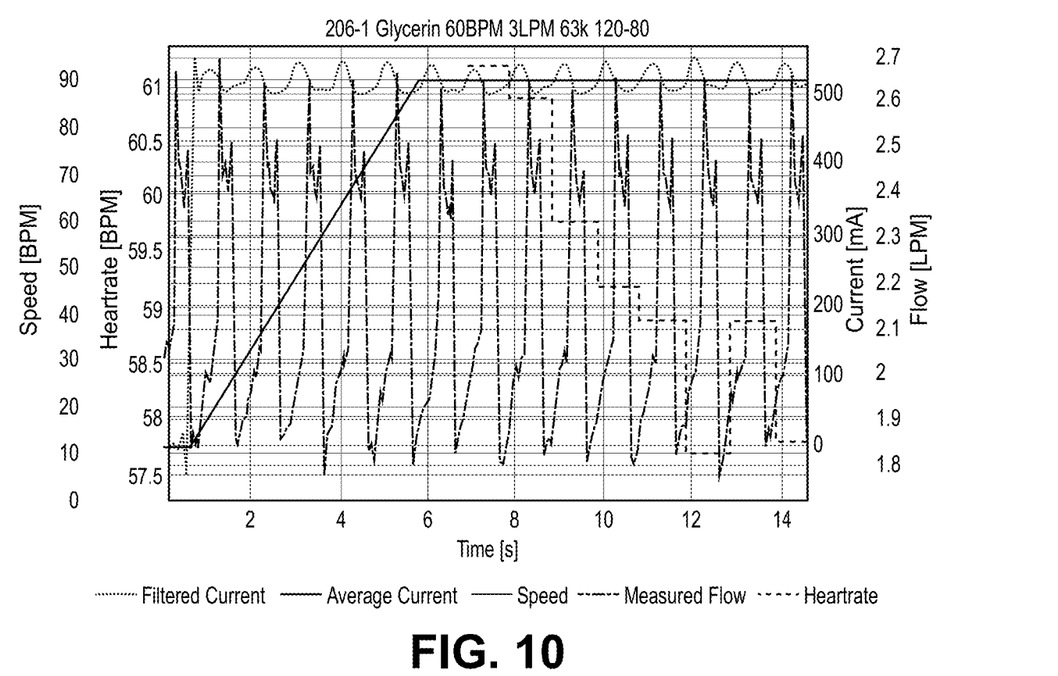
FIG. 10 illustrates exemplary device startup data tracings according to one embodiment of the present invention.

The startup tracings chart in FIG. 10 illustrates a startup test case wherein an exemplary electric motor is initiated to rotate an impeller within a blood pump, in combination with a sensing and controlling unit as that general system is described supra. The sensed and traced data may be sensed and traced by a sensor and/or processor and displayed on a display. As shown, filtered current starting at lower left then ramping up rapidly to pulse across the top of the chart) is pulsatile and in sync with measured blood flow. Thus, a peak in current results in a subsequent peak in blood flow, and a peak in current results in a subsequent peak in the measured blood flow—as described above, the motor current and blood flow are related. FIG. 10 is showing measured blood flow and filtered current. The digital filter applied to current causes a delay in that signal relative to unfiltered signals, e.g., blood flow. Thus, a peak in current (unfiltered) is actually nearly simultaneous with the blood flow peak. A peak in filtered current, then, corresponds with the preceding blood flow peak. Average current is illustrated as ramping steadily up from left to right, then flattening out across the top of the chart, effectively averaging the current pulses.

As illustrated, once the current begins crossing average current, heart cycles are delineated by positive (rising) crossings of average current, and heart rate measurement which is illustrated by the data beginning approximately midway through the current tracings and a slight ramping down to a regular heart rate interval at bottom right of the chart of FIG. 10.

Figure 11:
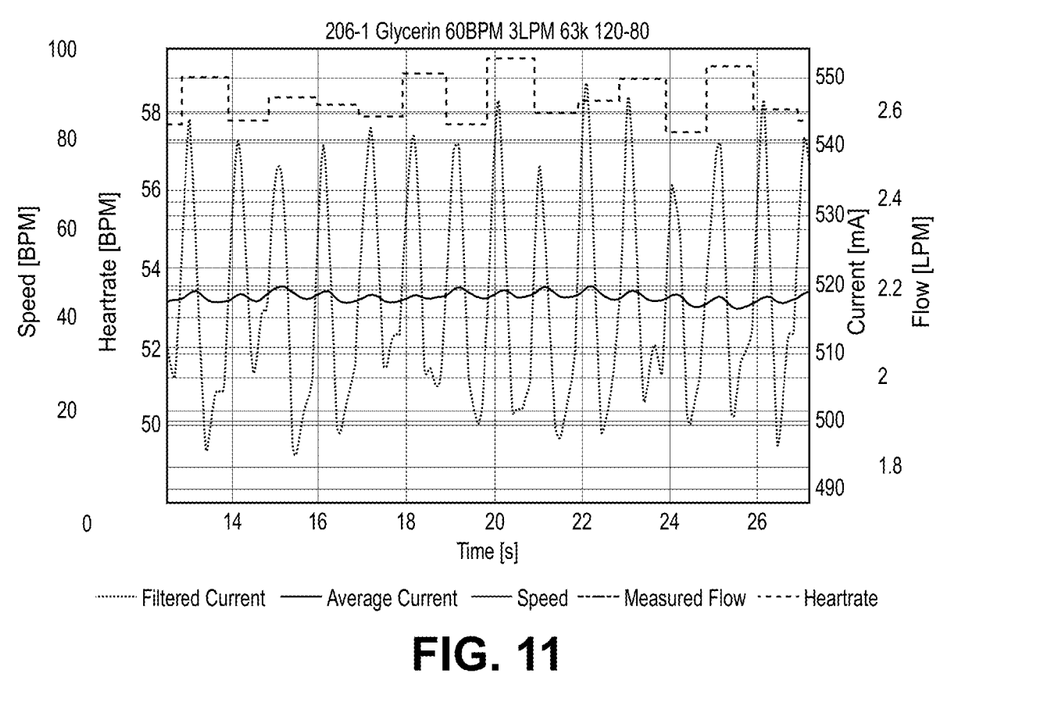
FIG. 11 illustrates exemplary device data tracings during normal running according to one embodiment of the present invention.

Normal running tracings are shown in FIG. 11, where motor current continues to periodically cross average current (the data cutting through the motor current tracing). Heart rate (data across upper portion of FIG. 11) updates at the end of each cycle, defined as the point at which current crosses its own average and is increasing.

Definition of valid pulsatility data: Heart rate is between an exemplary at least 30 and at least 180 bpm and/or exemplary peak-to-peak current is above at least 10 mA. Other thresholds may be employed for both heart rate and peak-to-peak current as the skilled artisan will recognize, all of these thresholds are within the scope of the present invention.

In the normal example of FIG. 11, heart rate is approximately 58 bpm and the peak-to-peak current is approximately 40 mA, both of which meets the exemplary validity criteria and, therefore, the flow rate generated by the blood pump is considered "valid".

Figure 12:
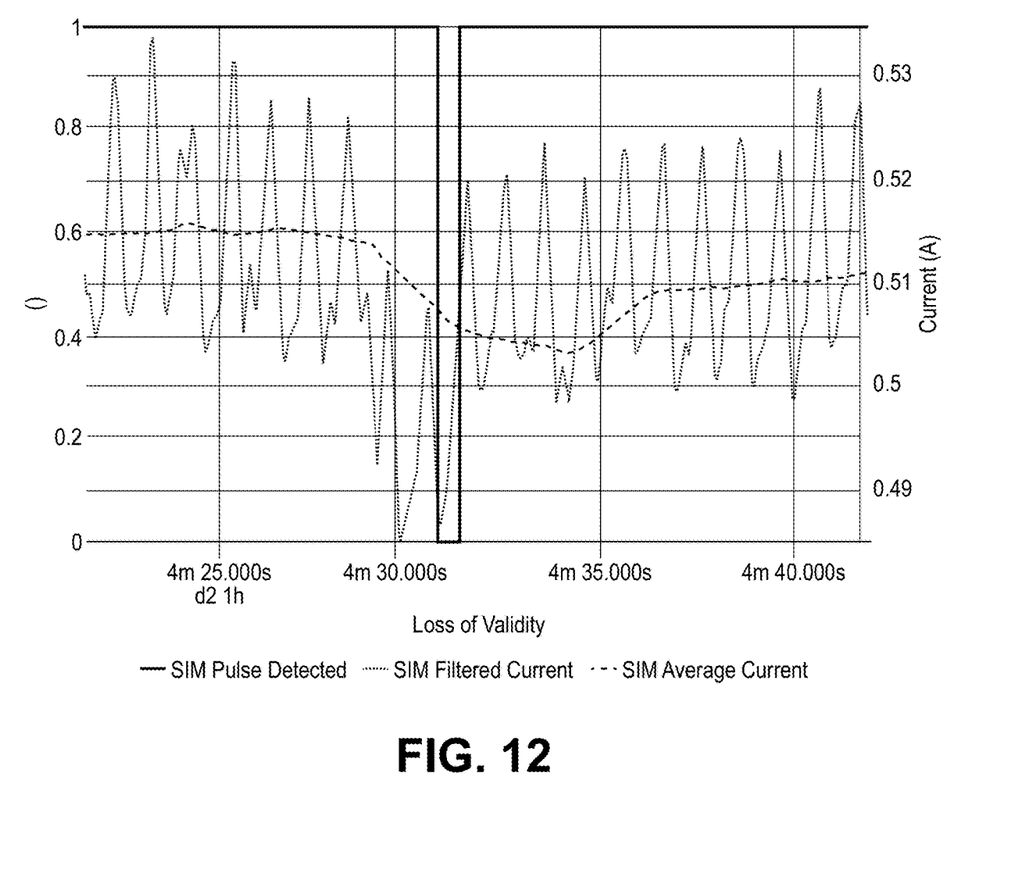
FIG. 12 illustrates an exemplary loss of validity according to one embodiment of the present invention.

Turning now to FIG. 12, validity of pulsatility is lost according to the above definition of valid pulsatility data. Midway through the chart of FIG. 12, current drops and does not rise above/cross its own average for several cycles. This, in turn, results in an apparent heart rate that is slowed and falls out of range, i.e., below the exemplary lower threshold of 30 bpm. The delineating lines indicate loss of validity of the flow rate and pulsatility for approximately one heart cycle.

A number of factors may cause loss of validity, including but not limited to, a transient in the motor current, pulse was too fast or too slow, noise in the current signal may appear as a "fast" pulse, and/or the amplitude of current waveform is too low, and/or movement of the patient.

The sensing and control unit described above may function to sense the data, trace the sensed data and monitor effectively in real time for validity and loss of validity.

Generally, loss of validity of pulsatility, flow rate and/or heart rate may occur on a transient basis and may simply correct itself. In other cases, the loss of validity may persist and require intervention to correct. Loss of validity as described above in either heart rate and/or motor current and/or pulsatility may be displayed on the display to allow the operator to detect and/or monitor.

If the invalidity of pulsatile blood flow, heart rate and/or pulsatility persists for a predetermined period of time, an alarm may be actuated to alert the medical professional. The alarm may be auditory and/or visual and may be in operative communication with the sensing and control unit, e.g., a display and/or speaker may be used to communicate the alarm. In some embodiments, the alarm may need to be turned off by an operator and, in other embodiments, the alarm may reset itself after a predetermined time or if the processor determines that the pulsatile blood flow data has returned to validity.

The alarm may be activated immediately upon a determination of invalidity of pulsatile blood flow, e.g., after one, or more than one, current peak is determined to be below the current peak low threshold. In other embodiments, the alarm may activate only if the invalid pulsatile blood flow condition, e.g., low current peak values and/or heart rate outside of predetermined upper or lower thresholds, persists for a predetermined period of time, e.g., 8 seconds. In some embodiments, if the current peak values and/or heart rate values return to validity for more than a predetermined time, e.g., 4 seconds, then the alarm may be deactivated. The time to activate and/or deactivate the alarm is well within the purview of the skilled artisan. Accordingly, the predetermined times to activate and deactivate the alarm are merely exemplary.

In certain embodiments, the sensing and control unit may be configured to capture and store a baseline data set that may include one or more of a baseline heart rate/pulse rate, peak-to-peak average and/or blood flow rate over a predetermined number of pulses and/or motor current peak values and/or over a predetermined amount of time. During implanted operation of the blood pump, the operator may determine that the patient is sufficiently stable to justify capturing and storing the baseline data. This may be achieved by provision of an element that is actuable by an operator. e.g., a button on the device or on the display screen, such that when actuated, the relevant baseline data is captured and stored. The stored baseline data may then be used during subsequent operation of the subject blood pump as a reference against which real-time data, e.g., heart rate and/or motor peak-to-peak current magnitudes, are measured. In this manner, a patient-specific reference alarm may be employed wherein the alarm as described above, may be actuated if the patient's heart rate and/or peak-to-peak motor current and/or blood flow rate values fall below a predetermined amount, relative to the stored baseline data. For example, a predetermined percentage drop, or a specific magnitude drop, of the real-time patient data from the stored baseline data may be provided for use by the processor in assessing whether to actuate the alarm.

This approach may be used alone or in combination with the alarm-triggering or actuating systems described above.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A medical device having a sensing and control unit that is configured to determine flow rate of blood through a blood pump that is temporarily or permanently implanted in a patient's vasculature, the blood pump having an impeller adapted to be rotationally driven by an electric motor, the sensing and control unit comprising:
   a current sensor configured to sense the peak-to-peak current generated by the electric motor;
   a processor operatively connected with the current sensor and with the electric motor, and configured to determine the rotational speed of the electric motor, and to receive the sensed peak-to-peak current data; and
   a memory operatively connected with the processor,
   wherein the determined rotational speed of the electric motor is associated with the sensed peak-to-peak current data, and
   further wherein the processor is configured to determine blood flow rate based on the obtained peak-to-peak current data and the associated determined rotational speed data at one or more points during operation of the blood pump
   the memory comprises a predetermined current peak low threshold and the processor is configured to determine whether a magnitude of each received current peak is greater than the predetermined current peak low threshold during operation of the implanted blood pump, the processor is configured to determine that the pulsatility of blood flow is valid if each of the magnitudes of the received plurality of current peaks is above the predetermined current peak low threshold, and the processor is configured to determine that the pulsatility of blood flow is invalid if one, or more than one, of the magnitudes of the received plurality of current peaks is below the predetermined current peak low threshold.

2. The medical device of claim 1, wherein the peak-to-peak current data is obtained for each cardiac cycle of the patient's heart.

3. The medical device of claim 2, wherein the determined flow rate is obtained for each cardiac cycle of the patient's heart.

4. The medical device of claim 1, wherein the determined blood flow rate does not require calibration of the medical device, or calibration of the medical device to the patient.

5. The medical device of claim 4, wherein the determined flow rate is independent of temperature, drive shaft friction, and other time-varying characteristics of the device.

6. The medical device of claim 1, further comprising a drive shaft rotationally connected at a proximal end to the electric motor and rotationally connected at a distal end to the impeller, wherein the electric motor is not implanted within the patient's vasculature.

7. The medical device of claim 1, further wherein the electric motor is implanted within the patient's vasculature and rotationally coupled to the impeller.

8. The medical device of claim 1, wherein the determined flow rate is independent of an absolute motor current value.

9. The medical device of claim 1, further comprising a display in operative communication with the sensing and control unit, wherein one or more of the obtained peak-to-peak current data, associated rotational speed, and the determined flow rate is displayed.

10. The medical device of claim 1, wherein the blood pump comprises a vascular assist device.

11. The sensing and control unit of claim 10, wherein the vascular assist device comprises a left ventricular assist device or a right ventricular assist device.

12. The medical device of claim 11, wherein the blood pump comprises a housing that is at least partially expandable or is non-expandable.

13. The medical device of claim 1, wherein the processor is further configured to receive heart rate data associated with the patient and that is correspondent with the received peak-to-peak current data, the processor further configured to determine whether the received heart rate is within predetermined upper and lower thresholds during operation of the implanted blood pump, and wherein the processor is configured to determine that the pulsatility of blood flow is valid if the received current peak is determined to be above the predetermined current peak low threshold, and the correspondent received heart rate data also is determined to be within the predetermined upper and lower heart rate thresholds.

14. The medical device of claim 13, wherein the processor is configured to determine that the pulsatility of blood flow is invalid if at least one of the received current peaks is determined to be below the predetermined current peak low threshold, and/or the associated received heart rate data also is determined to be outside of the predetermined upper and lower heart rate thresholds.

15. The medical device of claim 14, wherein the processor is configured to determine that the pulsatility of blood flow is invalid if the received heart rate data is determined to be outside of the predetermined heart rate upper or lower thresholds for a predetermined period of time, and the predetermined current peak threshold is also determined to be below the predetermined current peak low threshold for a predetermined period of time.

16. The medical device of claim 15, wherein the processor is configured to actuate an alarm that is annunciated by one or more of an audio, visual and/or tactile stimulus if the received heart rate is determined to be below the predetermined heart rate low threshold.

17. The medical device of claim 15, wherein the processor is operatively connected with a display and configured to display a message on the display if at least one received current peak is below the predetermined current peak low threshold and/or the received heart rate is determined to be below the predetermined heart rate low threshold.

18. The medical device of claim 13, wherein the predetermined heart rate lower threshold is at least 30 beats per minute and the predetermined heart rate upper threshold is 180 beats per minute or less.

19. The medical device of claim 1, wherein the processor is configured to determine that the pulsatility of blood flow is invalid if the received current peaks are determined to be below the predetermined current peak threshold for a predetermined number of current peaks and/or a predetermined period of time.

20. The medical device of claim 1, wherein the predetermined current peak low threshold is 10 mA or greater.

21. The medical device of claim 1, wherein the processor is configured to actuate an alarm that is annunciated by one or more of an audio, visual and/or tactile stimulus if at least one of the received current peaks is determined to be below the predetermined current peak low threshold.

22. A method for establishing a patient-specific baseline data set for an implanted blood pump, comprising:
providing the medical device of claim 1;
monitoring the peak-to-peak motor current values and/or blood flow rate values;
determining that the monitored values are stable values;
determining a baseline data set for the stable values;
storing the baseline data set in the sensing and control unit;
determining a patient-specific alarm trigger comprising a magnitude value drop or a percentage drop below the stored baseline data set that will trigger an alarm;
continuing operation of the implanted blood pump with real-time monitoring of the peak-to-peak motor current values and/or blood flow rate values;
comparing the monitored real-time peak-to-peak motor current values and/or blood flow rate values against the stored baseline data set; and
triggering the alarm if the monitored real-time peak-to-peak motor current values and/or blood flow rate values drop below the patient-specific alarm trigger.

23. A sensing and control unit for determining validity of pulsatility of blood flow through a blood pump that is temporarily or permanently implanted in a patient's vasculature, the blood pump having an impeller adapted to be rotationally driven by an electric motor, the sensing and control unit comprising:
a current sensor operatively connected with the electric motor and configured to sense peak-to-peak current generated by the electric motor;

a processor in operative connection with the current sensor and configured to receive sensed data from the current sensor comprising a plurality of current peaks, wherein the processor is configured to determine whether each received current peak is greater than a predetermined current peak low threshold during operation of the implanted blood pump, wherein the processor is configured to determine that the pulsatility of blood flow is valid if each of the received plurality of current peaks is above the predetermined current peak low threshold, and wherein the processor is configured to determine that the pulsatility of blood flow is invalid if one, or more than one, of the received plurality of current peaks is below the predetermined current peak low threshold; and an alarm in operative connection with the processor, wherein the alarm is activated if the invalid pulsatility of blood flow is determined and persists for a predetermined period of time and/or a predetermined number of current peaks, wherein the alarm comprises an audio, visual and/or tactile stimulus.

24. The sensing and control unit of claim 23, wherein the processor is further configured to receive heart rate data associated with the patient and correspondent with the received current data to determine whether the received heart rate is within predetermined upper and lower thresholds during operation of the implanted blood pump, wherein the processor is configured to determine that the pulsatility of blood flow is invalid if the received current peak is below the predetermined current peak low threshold, and the correspondent received heart rate data also is not within its predetermined upper and lower thresholds, and wherein the alarm is activated if the invalid pulsatility of blood flow is determined and persists for a predetermined period of time and/or a predetermined number of current peaks, wherein the alarm comprises an audio, visual and/or tactile stimulus.

25. A medical device having a sensing and control unit that is configured to determine flow rate of blood through a blood pump that is temporarily or permanently implanted in a patient's vasculature, the blood pump having an impeller adapted to be rotationally driven by an electric motor, the sensing and control unit comprising:

a current sensor configured to sense the peak-to-peak current generated by the electric motor;

a processor operatively connected with the current sensor and with the electric motor, and configured to determine the rotational speed of the electric motor, and to receive the sensed peak-to-peak current data; and a memory operatively connected with the processor, wherein the determined rotational speed of the electric motor is associated with the sensed peak-to-peak current data, and further wherein the processor is configured to determine blood flow rate based on the obtained peak-to-peak current data and the associated determined rotational speed data at one or more points during operation of the blood pump and the processor is configured to obtain peak-to-peak current data for each cardiac cycle of the patient's heart.

\* \* \* \* \*